US012280935B2

(12) United States Patent
Crouthamel et al.

(10) Patent No.: US 12,280,935 B2
(45) Date of Patent: Apr. 22, 2025

(54) LEATHER PROTECTIVE STORAGE DEVICE

(71) Applicants: Barbara Crouthamel, Youngstown, NY (US); Blake Leon, Youngstown, NY (US)

(72) Inventors: Barbara Crouthamel, Youngstown, NY (US); Blake Leon, Youngstown, NY (US)

( * ) Notice: Subject to any disclaimer, the term of this patent is extended or adjusted under 35 U.S.C. 154(b) by 0 days.

(21) Appl. No.: 18/637,964

(22) Filed: Apr. 17, 2024

(65) Prior Publication Data

US 2024/0343464 A1    Oct. 17, 2024

Related U.S. Application Data

(60) Provisional application No. 63/496,543, filed on Apr. 17, 2023.

(51) Int. Cl.
| | |
|---|---|
| *A61L 2/26* | (2006.01) |
| *A61L 2/08* | (2006.01) |
| *B65D 25/08* | (2006.01) |
| *B65D 25/28* | (2006.01) |
| *B65D 43/16* | (2006.01) |
| *B65D 81/26* | (2006.01) |
| *B65D 81/30* | (2006.01) |

(52) U.S. Cl.
CPC ............ *B65D 81/266* (2013.01); *A61L 2/084* (2013.01); *A61L 2/26* (2013.01); *B65D 25/08* (2013.01); *B65D 25/2826* (2013.01); *B65D 43/163* (2013.01); *B65D 81/30* (2013.01); *A61L 2202/11* (2013.01); *A61L 2202/122* (2013.01); *A61L 2202/26* (2013.01)

(58) Field of Classification Search
CPC . B65D 81/30; A61L 2/084; A61L 2/26; A61L 2202/11; A61L 2202/122; A61L 2202/26
See application file for complete search history.

(56) References Cited

U.S. PATENT DOCUMENTS

2022/0341086 A1\* 10/2022 Jang ..................... B01D 53/266

FOREIGN PATENT DOCUMENTS

| CN | 107296396 A | \* 10/2017 |
|---|---|---|
| CN | 107485182 A | \* 12/2017 |
| CN | 206792328 U | \* 12/2017 |

OTHER PUBLICATIONS

Translation of CN-107296396-A (Year: 2017).\*
Translation of CN-206792328-U (Year: 2017).\*
Translation of CN-107485182-A (Year: 2017).\*

\* cited by examiner

*Primary Examiner* — Sean E Conley
(74) *Attorney, Agent, or Firm* — Dunlap Bennett & Ludwig, PLLC; Anna L. Kinney

(57) ABSTRACT

A storage device for protecting delicate objects from environmental elements includes an enclosed housing having a base, sidewalls, a top, and a hinged door. At least one slotted compartment mounted within the housing houses a humidity control device. At least one odor control packet is mounted to the interior of the housing. The storage device can be subdivided into at least two unequal volumes by a removable perforated shelf, including a first volume for storing delicate objects and a second volume housing the LED germicidal light, which can emit anti-microbial light. The first volume can be further subdivided by a removable perforated partition.

11 Claims, 4 Drawing Sheets

LEATHER PROTECTIVE STORAGE DEVICE

CROSS-REFERENCE TO RELATED APPLICATION

This application claims the benefit of priority of U.S. provisional application No. 63/496,543, filed Apr. 17, 2023, the contents of which are herein incorporated by reference.

BACKGROUND OF THE INVENTION

The present invention relates to leather goods and, more particularly, to a leather protective storage device.

Today designer handbags and shoes are seen as investments. Leather is a three-dimensional fiber and has breathing properties even with finish on it. It either gives up moisture or it absorbs moisture. Leathers are optimally treated with fungicides and anti-mold agents at the tannery but once the leather article is in use, it encounters humidity, sunlight, and other airborne contaminants such as acid rain. Leather goods often suffer from mold, mildew, and bacteria growth as well as drying out. High moisture content in the air (humidity) and lack of light are the main causes of mold growth on leather goods. Keeping leather at a temperature of 50-70° Fahrenheit and relative humidity (RH) of 30 to 60% is ideal.

Avoiding dampness and bacterial contamination is of utmost importance. Exposure to excess moisture is known to have undesirable and detrimental effects on leather handbags and leather articles when they are stored for significant periods of time, such as six months or more. This causes a mustiness on the leather. Not only does mustiness leave an unpleasant odor but mold growth tends to weaken the natural fibers and produces allergens to trouble those with allergies.

Currently available storage containers do not deal with the fact that leathers give off moisture and absorb moisture creating mold issues and, in some cases, may even add to the problem by enclosing the leather handbag in its own moisture, causing leather to grow mold on its surface or inside the lining. Plain boxes or plastic bins are useful for storage but do not effectively deal with the mold and mildew problem created in humid dark spaces or the drying out of leather in dry spaces. A typical bin or container doesn't offer any protection from mold and mildew; nor do any containers in the market sanitize these leather articles. Also, other storage units do not protect them from potential drying out of said articles in dry arid climates. Handbag dust bags or sleepers made of fabric have long been widely used to keep dust and other particulate matter from handbags, and cardboard boxes are used to protect shoes. However, these bags and boxes are open to rapid changes in the temperature and humidity of ambient air, and thus are ineffective in dealing with high humidity or changes in the humidity to which the handbags are exposed.

As can be seen, there is a need for a means of preserving and protecting leather goods during storage that prevents mold, mildew, drying, and cracking.

SUMMARY OF THE INVENTION

The present invention provides a storage unit for leather goods that combines a light emitting diode (LED) emitting germicidal light with compartments for humidity controlling packets and odor control packets. The storage unit is particularly useful for handbags, shoes, and accessories.

In one aspect of the present invention, a leather protective storage device is provided which includes an enclosed housing having a base, sidewalls, a top, with a door hingedly coupled to at least one of the base, sidewalls, and top. The enclosed housing can include at least one slotted compartment or pocket mounted to an interior of the housing, with a humidity control device housed therein. At least one LED is mounted to an interior of the housing.

The LED(s) can sanitize leather material when powered on. For example, the LED(s) may be mounted on a base of the housing, positioned such that an article stored within the housing is not directly in contact with the light therefrom.

In another aspect of the present invention, a leather protective storage device is provided which includes an enclosed housing with an interior volume sufficient to store leather goods or other goods. The enclosed housing can include at least one perforated compartment mounted on an interior wall, which can be configured to store a humidity control device. The housing can include a perforated shelf, tray, or floor mounted on the housing's sidewalls, which can subdivide the housing into two unequal volumes. A perforated vertical divider or partition can be mounted to the sidewalls and to the perforated shelf to further subdivide the interior volume of the housing into equal or unequal volumes depending upon the articles to be stored. The housing can include at least one LED mounted to an interior portion thereof, which can sanitize leather material when powered on.

The container disclosed herein may be used to store and protect a variety of articles, such as handbags, antiques, artifacts, and collectibles.

These and other features, aspects and advantages of the present invention will become better understood with reference to the following drawings, description, and claims.

DETAILED DESCRIPTION OF THE INVENTION

Figure 1:
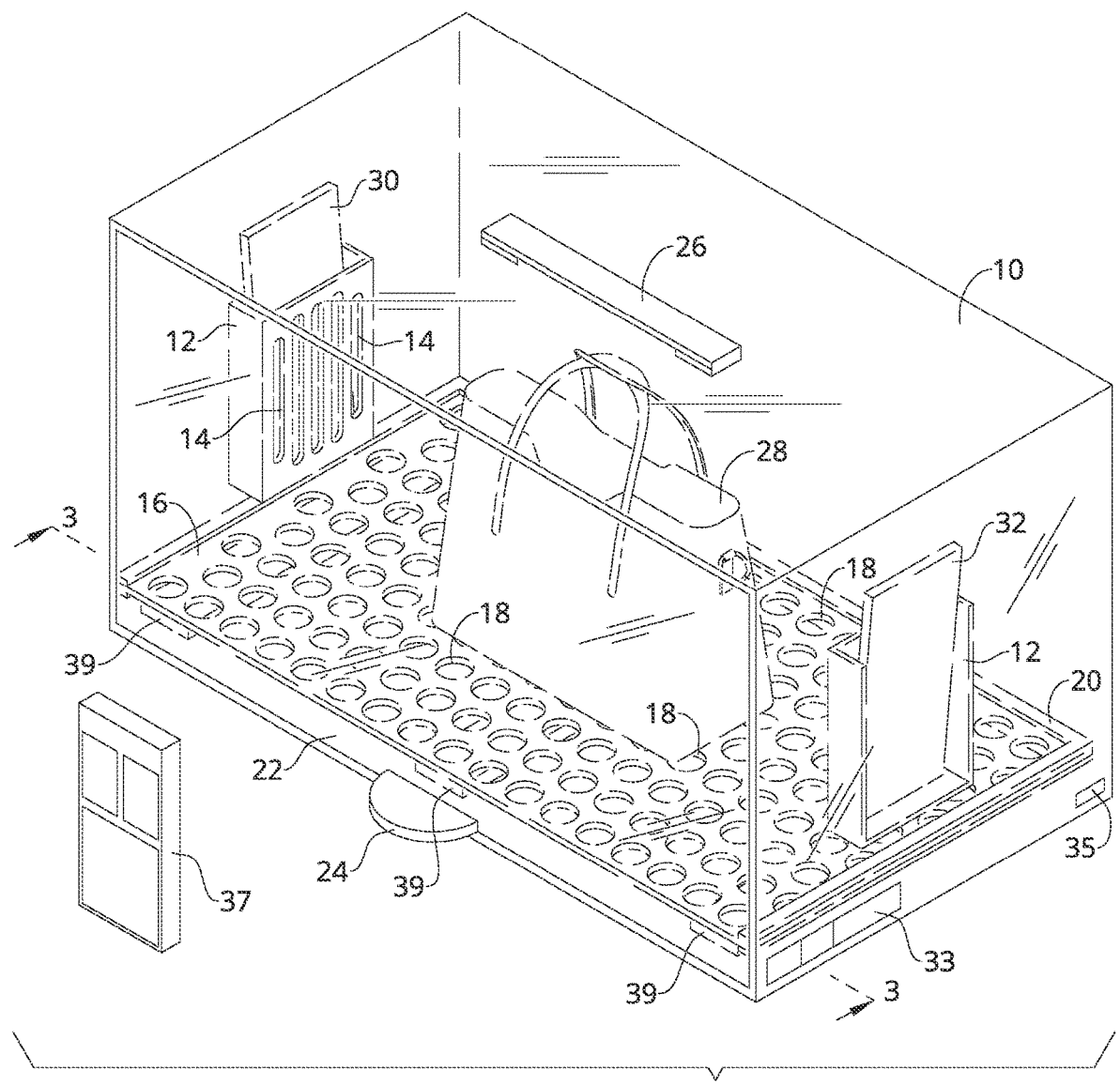
FIG. 1 is a perspective view of a storage unit according to an embodiment of the present invention, shown in use.

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Broadly, an embodiment of the present invention provides a storage container housing one or more humidity control devices which maintains a generally constant relative humidity (RH) despite ambient humidity swings, likened to a handbag and shoe humidor.

LED germicidal light has bacteria and virus eliminating properties and may be utilized for sanitization purposes, e.g., to help kill bacteria. The container of the present subject matter may have walls that are transparent to the visible light spectrum and opaque to ultraviolet light. In some cases, the container may have UV-blocking material applied to the container walls.

In some embodiments, the container may be fitted with one or more LED along the base and/or inside walls of the container. The LED may be a light strip glued to an interior of the container, a light bar, a light tape, a wand, and/or small individual stick-on lights. The LED may be powered by a battery pack. A power supply and/or recharging unit may be included. A user may access the power supply, battery, or recharging unit of the LED from outside of the container. The LED(s) may be antimicrobial, such as antibacterial and/or antifungal. For example, the LEDs may emit light at wavelengths between about 380-750 nm.

In some embodiments, the container may have a vertical perforated divider or wall, enabling a single container to have multiple compartments to separately protect multiple articles. Storing articles in separate compartments may be desirable, for example, to prevent dye transfer between articles. The dividers may be removable in some cases.

In some embodiments, the inventive container or storage unit may comprise multiple compartments or receptacles. The compartments may house or carry a humidity/moisture control packet, an odor control/odor eliminating packet or an odor absorbing wick, and/or an LED. The humidity control packet and the odor eliminating packet may be housed in the same compartment. The humidity control packet compartment may have perforations or openings to enable air flow and may be accessible to a user so that the humidity control packet is easily removed and replaced.

In some embodiments, odor removing packets or odor absorbing wicks may be provided within the container to combat odors such as smoke, perfume, and the like and keep the leather from developing a musty odor.

The packets may be accessible from outside the container for easy replacement. Alternatively, the packets may be located under a perforated floor at a bottom of the container. A divider may separate the packets and the LED.

The utilization of an LED inside the unit and compartments to house humidity controlling packets and "odor removing" packets enables leather goods stored in the device to breathe, absorb and eliminate moisture, and be exposed to light acting as a sanitizing component that prevents the growth of mold. This protects the leather goods from contaminants and prevents them from drying out or cracking. The moisture control and LED may work alone or in combination to protect leather goods stored inside of the container. The container also prevents leather goods from dye transfer from fabrics or other leather goods that may lean against them in storage. Leather goods stored inside of the container may include but are not limited to handbags, shoes, artwork, and jackets.

The present invention may restore leather by restoring a predetermined relative humidity, killing bacteria with sanitizing LED light, disinfecting the leather, and preventing said articles from drying out.

The composition of the container is not particularly limited by the present invention provided the materials generally have low water vapor transmission rates. For example, the container may be composed of plastic, acrylic, glass, and/or polycarbonate, such as clear glass or acrylic sidewalls with wood trim.

The shape of the container is not particularly limited by the present invention. For example, the container may be shaped as a cube, a rectangular cuboid, or in the shape of a handbag. In some embodiments, the container may be configured with an upper dome.

The inventive storage unit may be kept in a closet, a garage, or in a cargo unit such as a shipping container used to ship goods overseas. Overseas shipping in these unique containers may dramatically reduce the rate of leather handbags being disposed of due to the presence of mold spores and the strong smell of mildew. The storage unit may also be used to display leather goods in stores. The container may have transparent walls with ultraviolet light filtering capabilities to protect stored article. Therefore, the container may be placed in a window display, for example in a retail store, to slow the color fading and oxidation of the stored article over time.

In some embodiments, edges of the container may have silicone beading applied thereto to form an airtight seal.

The container may have a control panel with a power (on/off) switch, universal serial bus (USB) socket, processor, and/or charging socket for charging the LED germicidal light.

Referring now to FIGS. 1 through 6, FIG. 1 shows a storage container or housing 10 according to an embodiment of the present invention, dimensioned to accommodate leather goods such as the illustrated handbag 28. The housing 10 has a base, transparent plastic walls, a transparent top, and a transparent door 22. In embodiments, the transparent walls of the housing 10 and door 22 can be coated with material, such as film, to block ultraviolet light from penetrating storage container 10. A transport handle 26 mounted on top of the storage container 10 facilitates transport. In embodiments, a sliding shelf or floor 16 with holes, perforations, or apertures 18 may horizontally partition the housing into a first volume and a second volume, with most of the total volume being the first volume, configured to store leather goods 28. A second volume, smaller than the first volume, may be under the partition 16, for example, and configured to house a control panel 33, a USB or charging port 35, and lighting 39. The control panel may service commands wirelessly received from a remote control 37, such as power on/off commands to lighting 39 and control power distribution to/from USB and/or charging port 35. The lighting 39 can be anti-microbial lighting, such as LED germicidal lighting, to prevent, remove, and/or sanitize the handbag 28 while stored in storage container 10. For example, lighting 39 can prevent and/or kill bacteria, mold, and/or mildew formations on the handbag 28 and/or in the air circulating within the housing 10. The floor 16 allows airflow and prevents contact of the stored handbag 28 to the LED light 39.

Figure 2:
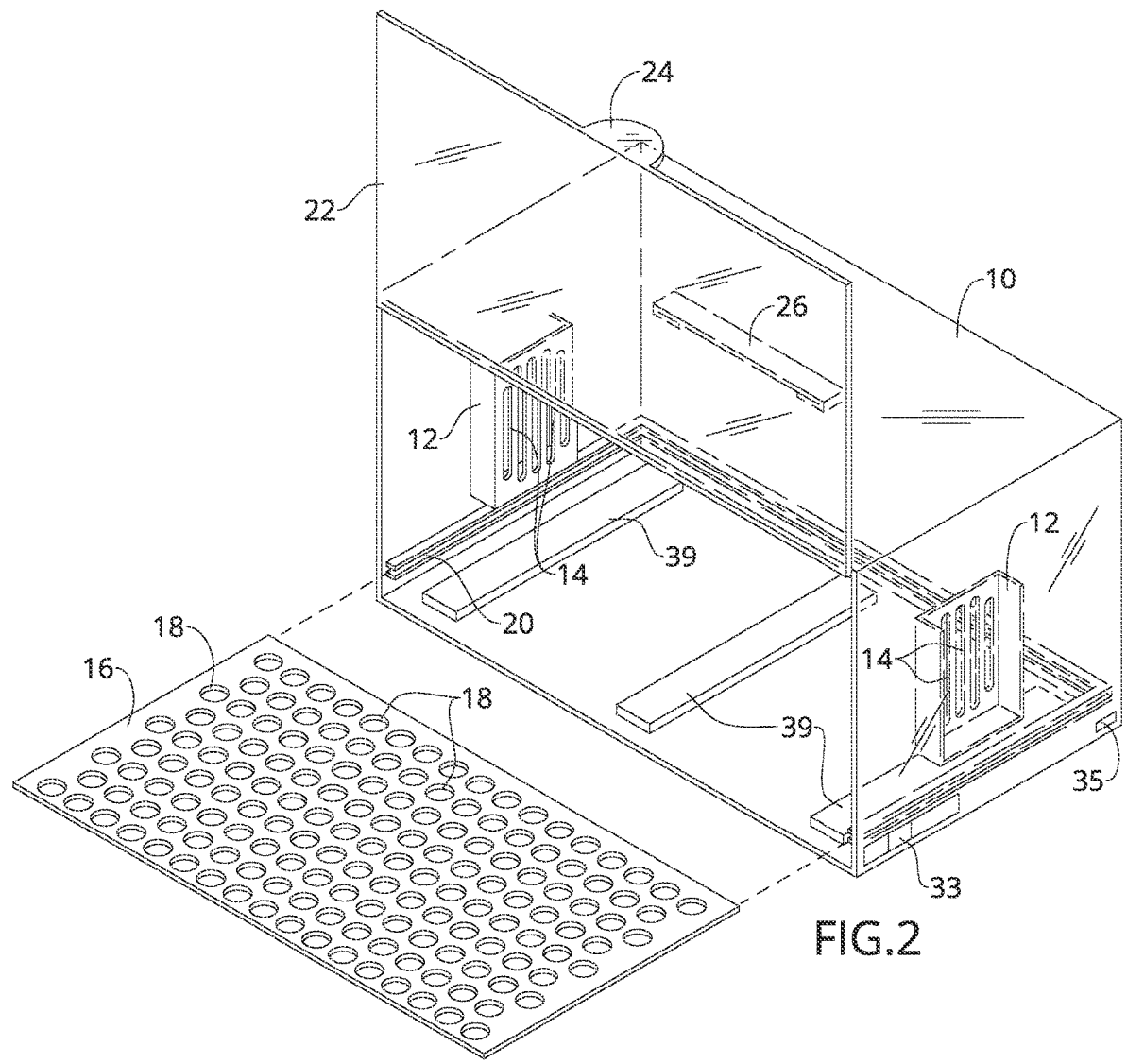
FIG. 2 is an exploded view thereof.

As shown in FIG. 2, the floor 16 may be slidably removed from a track or groove 20 of the housing 10. Slots 14 in compartments 12 facilitate air flow across their contents. The control panel 33 may actuate power and/or otherwise operate electronic and/or electromechanical components of storage device 10, such as the lighting 39 (switch on/off) and USB and/or charging port 35. The control panel 33 may operate or interface with a processor running a software application (not shown), in some cases.

Figure 3:
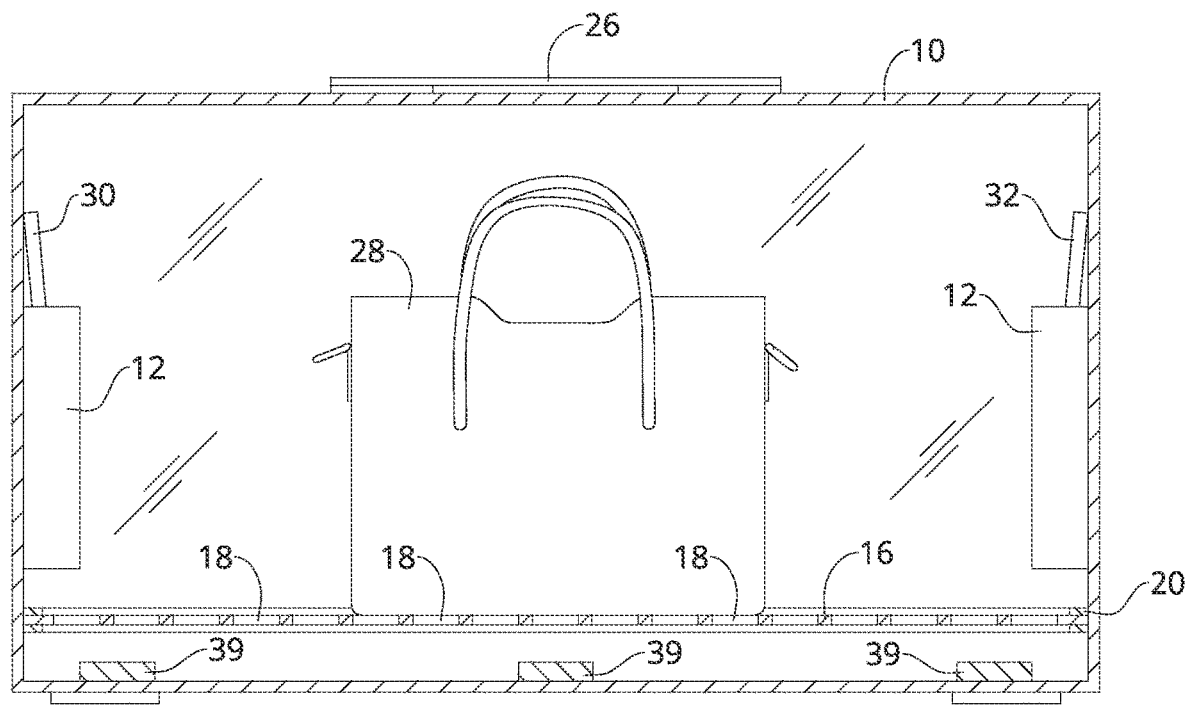
FIG. 3 is a sectional view thereof, taken along line 3-3 in FIG. 1, shown in use.

Turning to FIG. 3, the compartments 12 mounted on interior vertical surfaces of the storage container 10 may store a humidity control insert 30 and/or an odor control insert 32. In embodiments, the inserts may be humidity control packets 30 containing a composition operative to absorb moisture from air and/or odor control packets 32 containing a composition operative to conceal, absorb, or neutralize odors. The inserts 30, 32 may be interchangeable.

Figure 4:
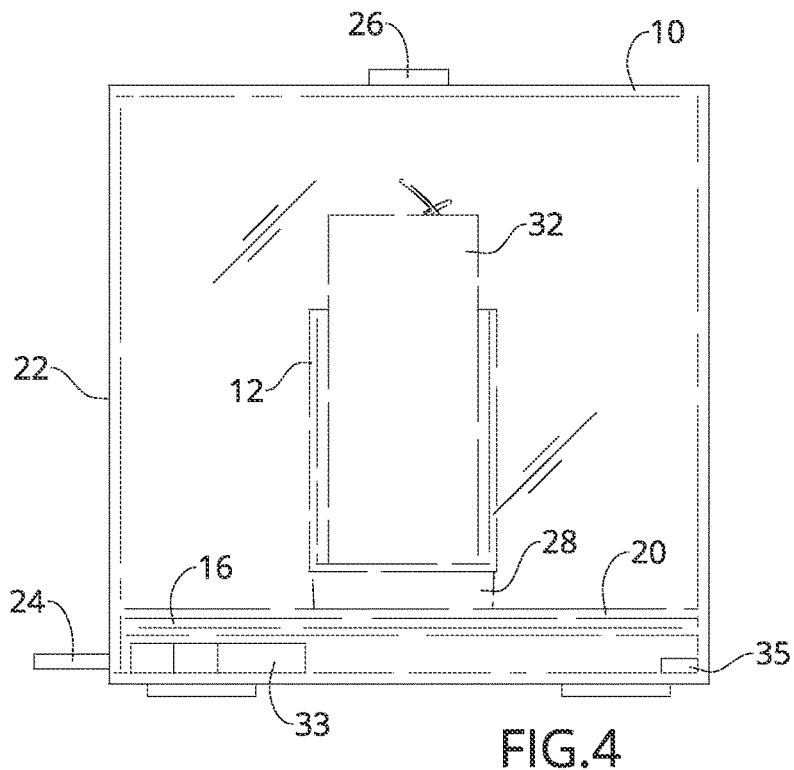
FIG. 4 is a side elevation view thereof.
Figure 5:
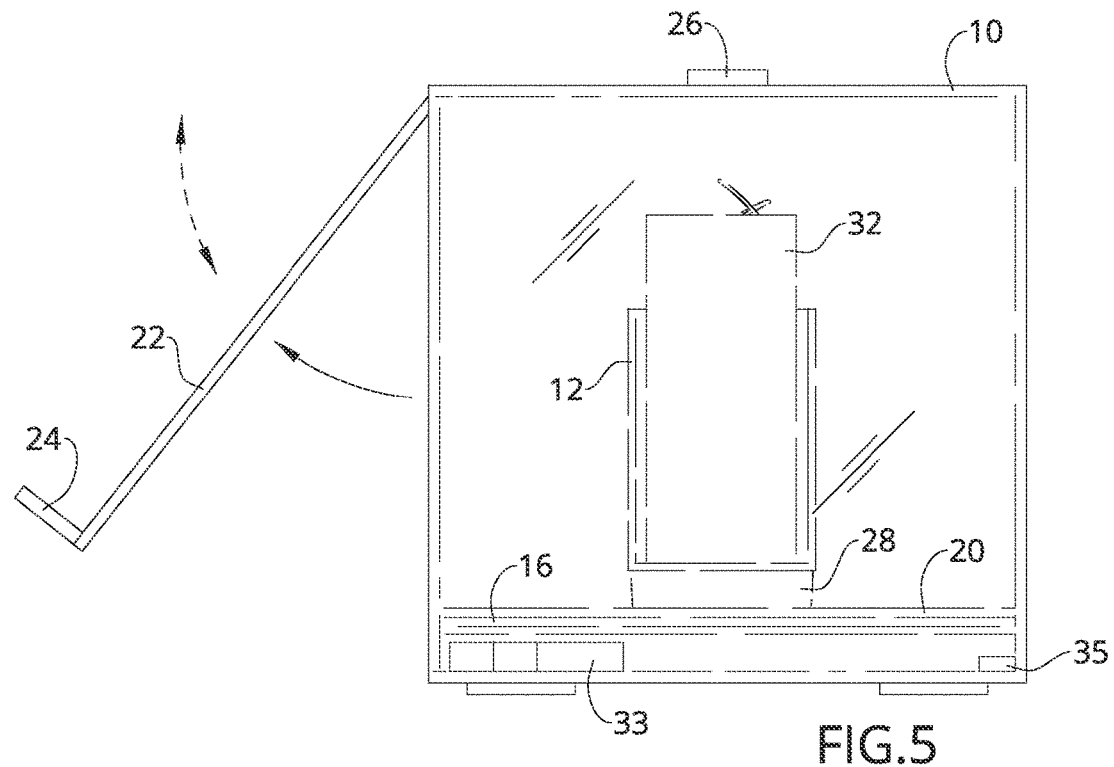
FIG. 5 is another side elevation view thereof, shown in an open position.

As shown in FIGS. 4 and 5, a transparent door 22, with a door handle 24 extending from a lower edge thereof, facilitates opening the storage container 10. In embodiments, usage of handle 24 to open storage container 10 can cause door 22 to hingedly move along an arc, illustrated in FIG. 5.

Figure 6:
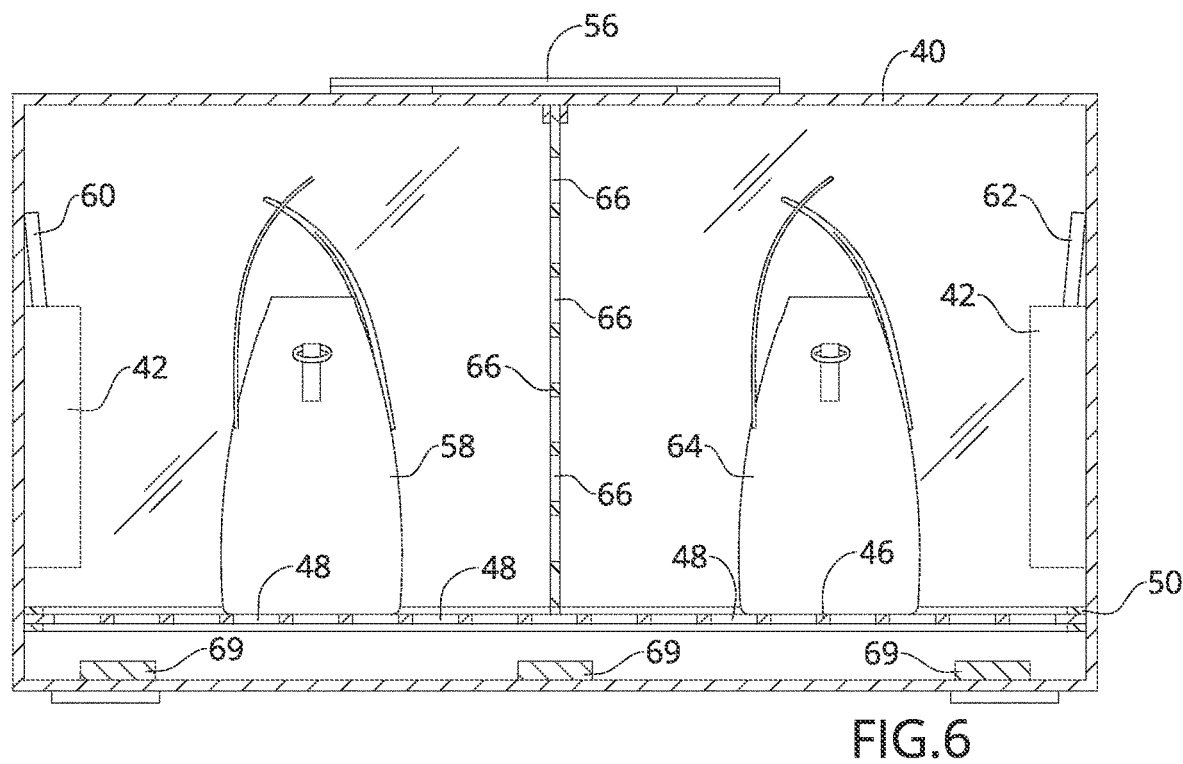
FIG. 6 is a sectional view of a storage unit according to another embodiment of the present invention, shown in use.

FIG. 6 is a cross-sectional view of an alternative embodiment of a storage container or housing 40, partitioned to accommodate multiple leather goods 58, 64, such as a handbag(s) and/or shoes. The number of compartments and the number and type of associated stored articles are not particularly limited. A handle 56 mounted on top of the storage container 40 facilitates transport. Slotted compartments 42 mounted on interior vertical surfaces of the storage container 40 may each accommodate a humidity control insert 60 and/or an odor control insert 62. The inserts 60, 62 may be interchangeable and may contain compositions operative to control humidity and/or control odor. A slidable shelf or tray 48 with perforations 46 formed therein can be removably installed using a track or groove 50 to partition storage container 40 into at least two, unequal, volumes. In embodiments, a first volume can comprise most of the total volume of storage container 40 and can be further subdivided by a vertical partition 66 having apertures 68 formed therein. The volume subdivided by the vertical perforated partition 66 can be configured to store collectibles or leather goods 58, 64, such as a handbag or shoe. A second volume, defined by shelf 48, can be a minority of the total volume of storage container 40 and can be configured to house at least LED lighting 69. In embodiments, anti-microbial lighting 69 is configured to sanitize leather goods 58, 64 while stored in storage container 40, i.e., to prevent, remove, and/or kill microorganisms such as bacteria, mold, and/or mildew formed on leather goods 58, 64.

It should be understood, of course, that the foregoing relates to exemplary embodiments of the invention and that modifications may be made without departing from the spirit and scope of the invention as set forth in the following claims.

What is claimed is:

1. A leather protective storage device, comprising:
    an enclosed housing having a base, sidewalls, and a top, with a door hingedly coupled to at least one of the base, the sidewalls, and the top;
    at least one slotted compartment mounted to an interior of the enclosed housing;
    a humidity control device housed within the at least one slotted compartment; and
    at least one light emitting diode (LED) mounted to the interior of the enclosed housing;
    wherein the enclosed housing is transparent to visible light and is opaque to ultraviolet radiation.

2. The leather protective storage device of claim 1, further comprising a perforated shelf mounted horizontally within the enclosed housing.

3. The leather protective storage device of claim 1, further comprising a perforated divider mounted vertically within the enclosed housing.

4. The leather protective storage device of claim 2, wherein the at least one LED is mounted on the base between the perforated shelf and the base.

5. The leather protective storage device of claim 1, wherein the LED is operative to emit light in an antimicrobial wavelength.

6. The leather protective storage device of claim 2, further comprising a track formed on the interior and wherein the perforated shelf is slidably mounted on the track.

7. The leather protective storage device of claim 1, further comprising an odor control device housed within the at least one slotted compartment.

8. The leather protective storage device of claim 1, further comprising a power actuator mounted within the enclosed housing, said power actuator being operative to selectively switch the at least one LED on and off.

9. The leather protective storage device of claim 1, further comprising a charging port or a universal serial bus (USB) port operative to power the at least one LED.

10. The leather protective storage device of claim 1, further comprising a handle mounted to an exterior of the enclosed housing.

11. A leather protective storage device, comprising:
    an enclosed housing having a base, sidewalls, and a top, with a door hingedly coupled to at least one of the base, the sidewalls, and the top, with an odor control device housed within the at least one slotted compartment;
    at least one slotted compartment mounted to an interior of the enclosed housing;
    a humidity control device housed within the at least one slotted compartment; and
    at least one light emitting diode (LED) mounted to the interior of the enclosed housing.

* * * * *